US012746117B2

(12) United States Patent
Bukin et al.

(10) Patent No.: US 12,746,117 B2
(45) Date of Patent: Sep. 29, 2026

(54) PROSTHETIC HEART VALVE

(71) Applicant: Edwards Lifesciences Corporation, Irvine, CA (US)

(72) Inventors: Michael Bukin, Pardes Hanna (IL); Nikolai Gurovich, Hadera (IL)

(73) Assignee: Edwards Lifesciences Corporation, Irvine, CA (US)

( * ) Notice: Subject to any disclaimer, the term of this patent is extended or adjusted under 35 U.S.C. 154(b) by 943 days.

(21) Appl. No.: 18/056,486

(22) Filed: Nov. 17, 2022

(65) Prior Publication Data

US 2023/0080070 A1 Mar. 16, 2023

Related U.S. Application Data

(63) Continuation of application No. PCT/US2021/032857, filed on May 18, 2021.

(Continued)

(51) Int. Cl.
*A61F 2/24* (2006.01)

(52) U.S. Cl.
CPC .......... *A61F 2/2418* (2013.01); *A61F 2/2415* (2013.01); *A61F 2220/0075* (2013.01)

(58) Field of Classification Search
CPC .................. A61F 2/2418; A61F 2/2415; A61F 2220/0075; A61F 2/2436; A61F 2/9517;

(Continued)

(56) References Cited

U.S. PATENT DOCUMENTS

| | | | |
|---|---|---|---|
| 30,912 | A | 12/1860 | Ende |
| 3,409,013 | A | 11/1968 | Berry |

(Continued)

FOREIGN PATENT DOCUMENTS

| | | | |
|---|---|---|---|
| CN | 215688786 | U | 2/2022 |
| DE | 0144167 | C | 9/1903 |

(Continued)

OTHER PUBLICATIONS

HR. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Suzette J Gherbi
(74) *Attorney, Agent, or Firm* — Klarquist Sparkman LLP

(57) ABSTRACT

A prosthetic valve has a radially expandable and compressible frame including a plurality of interconnected struts and a valvular structure including a plurality of leaflets configured to regulate the flow of blood through the prosthetic valve. The leaflets can have undulating cusp edge portions. The prosthetic valve further includes at least one connecting skirt having a shape that corresponds to the cusp edge portion of at least one leaflet. The connecting skirt can connect the cusp edge portion of the leaflet to at least one of the struts of the frame. The connecting skirt can include a first set of yarns intersecting with a second set of yarns. The first and second sets of yarns can extend at oblique angles relative to a longitudinal axis of the at least one strut.

18 Claims, 9 Drawing Sheets

Related U.S. Application Data

(60) Provisional application No. 63/026,866, filed on May 19, 2020.

(58) Field of Classification Search
CPC ............ A61F 2250/0028; A61F 2/2433; A61F 2/2412; A61F 2/2463; A61F 2/2466; A61F 2220/0025
See application file for complete search history.

(56) References Cited

U.S. PATENT DOCUMENTS

| | | | |
|---|---|---|---|
| 3,548,417 | A | 12/1970 | Ronnie et al. |
| 3,587,115 | A | 6/1971 | Donald |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goicoechea et al. |
| 6,338,740 | B1 | 1/2002 | Carpentier |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,527,979 | B2 | 3/2003 | Constantz et al. |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |
| 6,936,067 | B2 | 8/2005 | Buchanan |
| 7,018,406 | B2 | 3/2006 | Seguin et al. |
| 7,018,408 | B2 | 3/2006 | Bailey et al. |
| 7,096,554 | B2 | 8/2006 | Austin et al. |
| 7,225,518 | B2 | 6/2007 | Eidenschink et al. |
| 7,276,078 | B2 | 10/2007 | Spenser et al. |

(56) References Cited

U.S. PATENT DOCUMENTS 7,276,084 B2 10/2007 Yang et al.
7,316,710 B1 1/2008 Cheng et al.
7,318,278 B2 1/2008 Zhang et al.
7,374,571 B2 5/2008 Pease et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,585,321 B2 9/2009 Cribier
7,618,446 B2 11/2009 Andersen et al.
7,618,447 B2 11/2009 Case et al.
7,655,034 B2 2/2010 Mitchell et al.
7,785,366 B2 8/2010 Maurer et al.
7,959,665 B2 6/2011 Pienknagura
7,959,672 B2 6/2011 Salahieh et al.
7,993,394 B2 8/2011 Hariton et al.
8,029,556 B2 10/2011 Rowe
8,075,611 B2 12/2011 Millwee et al.
8,128,686 B2 3/2012 Paul et al.
8,167,932 B2 5/2012 Bourang et al.
8,291,570 B2 10/2012 Eidenschink et al.
8,348,998 B2 1/2013 Pintor et al.
8,449,606 B2 5/2013 Eliasen et al.
8,454,685 B2 6/2013 Hariton et al.
8,652,203 B2 2/2014 Quadri et al.
8,685,055 B2 4/2014 VanTassel et al.
8,747,463 B2 6/2014 Fogarty et al.
9,078,781 B2 7/2015 Ryan et al.
9,168,131 B2 * 10/2015 Yohanan ............... A61F 2/2412
9,393,110 B2 * 7/2016 Levi ...................... A61F 2/2433
9,974,650 B2 * 5/2018 Nguyen-Thien-Nhon ................. A61F 2/2418
11,224,509 B2 1/2022 Dasi et al.
11,654,023 B2 * 5/2023 Zamani ................. A61F 2/2412 623/2.11
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0143390 A1 10/2002 Ishii
2002/0173842 A1 11/2002 Buchanan
2003/0014105 A1 1/2003 Cao
2003/0040791 A1 2/2003 Oktay
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0024452 A1 2/2004 Kruse et al.
2004/0039436 A1 2/2004 Spenser et al.
2004/0078074 A1 4/2004 Anderson et al.
2004/0186558 A1 9/2004 Pavcnik et al.
2004/0186563 A1 9/2004 Lobbi
2004/0186565 A1 9/2004 Schreck
2004/0260389 A1 12/2004 Case et al.
2005/0010285 A1 1/2005 Lambrecht et al.
2005/0075725 A1 4/2005 Rowe
2005/0075728 A1 4/2005 Nguyen et al.
2005/0096736 A1 5/2005 Osse et al.
2005/0096738 A1 5/2005 Cali et al.
2005/0137686 A1 6/2005 Salahieh et al.
2005/0188525 A1 9/2005 Weber et al.
2005/0203614 A1 9/2005 Forster et al.
2005/0203617 A1 9/2005 Forster et al.
2005/0234546 A1 10/2005 Nugent et al.
2006/0004469 A1 1/2006 Sokel
2006/0025857 A1 2/2006 Bergheim et al.
2006/0058872 A1 3/2006 Salahieh et al.
2006/0074484 A1 4/2006 Huber
2006/0108090 A1 5/2006 Ederer et al.
2006/0149350 A1 7/2006 Patel et al.
2006/0183383 A1 8/2006 Asmus et al.
2006/0190074 A1 8/2006 Hill et al.
2006/0229719 A1 10/2006 Marquez et al.
2006/0235511 A1 10/2006 Osborne
2006/0259136 A1 11/2006 Nguyen et al.
2006/0259137 A1 11/2006 Artof et al.
2006/0287717 A1 12/2006 Rowe et al.
2007/0005131 A1 1/2007 Taylor
2007/0010876 A1 1/2007 Salahieh et al.
2007/0010877 A1 1/2007 Salahieh et al.
2007/0112422 A1 5/2007 Dehdashtian
2007/0162102 A1 7/2007 Ryan et al.
2007/0203503 A1 8/2007 Salahieh et al.
2007/0203575 A1 8/2007 Forster et al.
2007/0203576 A1 8/2007 Lee et al.
2007/0208550 A1 9/2007 Cao et al.
2007/0213813 A1 9/2007 Segesser et al.
2007/0233228 A1 10/2007 Eberhardt et al.
2007/0260305 A1 11/2007 Drews et al.
2007/0265700 A1 11/2007 Eliasen et al.
2008/0021546 A1 1/2008 Patz et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0208327 A1 8/2008 Rowe
2008/0243245 A1 10/2008 Thambar et al.
2008/0255660 A1 10/2008 Guyenot et al.
2008/0275537 A1 11/2008 Limon
2008/0294248 A1 11/2008 Yang et al.
2009/0118826 A1 5/2009 Khaghani
2009/0125118 A1 5/2009 Gong
2009/0157175 A1 6/2009 Benichou
2009/0276040 A1 11/2009 Rowe et al.
2009/0281619 A1 11/2009 Le et al.
2009/0287296 A1 11/2009 Manasse
2009/0287299 A1 11/2009 Tabor et al.
2009/0299452 A1 12/2009 Eidenschink et al.
2009/0319037 A1 12/2009 Rowe et al.
2010/0004735 A1 1/2010 Yang et al.
2010/0049313 A1 2/2010 Alon et al.
2010/0082094 A1 4/2010 Quadri et al.
2010/0100176 A1 4/2010 Elizondo et al.
2010/0168844 A1 7/2010 Toomes et al.
2010/0185277 A1 7/2010 Braido et al.
2010/0198347 A1 8/2010 Zakay et al.
2010/0204781 A1 8/2010 Alkhatib
2011/0015729 A1 1/2011 Jimenez et al.
2011/0022157 A1 1/2011 Essinger et al.
2011/0066224 A1 3/2011 White
2011/0137397 A1 6/2011 Chau et al.
2011/0218619 A1 9/2011 Benichou et al.
2011/0319991 A1 12/2011 Hariton et al.
2012/0030090 A1 2/2012 Johnston et al.
2012/0078356 A1 3/2012 Fish et al.
2012/0089223 A1 4/2012 Nguyen et al.
2012/0101571 A1 4/2012 Thambar et al.
2012/0123529 A1 * 5/2012 Levi ...................... A61F 2/2412 623/2.11
2012/0259409 A1 10/2012 Nguyen et al.
2013/0023985 A1 1/2013 Khairkhahan et al.
2013/0046373 A1 2/2013 Cartledge et al.
2013/0150956 A1 6/2013 Yohanan et al.
2013/0166017 A1 6/2013 Cartledge et al.
2013/0190857 A1 7/2013 Mitra et al.
2013/0274873 A1 10/2013 Delaloye et al.
2013/0310926 A1 11/2013 Hariton
2013/0317598 A1 11/2013 Rowe et al.
2013/0331929 A1 12/2013 Mitra et al.
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277417 A1 9/2014 Schraut et al.
2014/0277419 A1 9/2014 Garde et al.
2014/0277424 A1 9/2014 Oslund
2014/0277563 A1 9/2014 White
2014/0296962 A1 10/2014 Cartledge et al.
2014/0330372 A1 11/2014 Weston et al.
2014/0343670 A1 11/2014 Bakis et al.
2014/0343671 A1 11/2014 Yohanan et al.
2014/0350667 A1 11/2014 Braido et al.
2015/0073545 A1 3/2015 Braido
2015/0073546 A1 3/2015 Braido

(56) References Cited

U.S. PATENT DOCUMENTS

| | | | |
|---|---|---|---|
| 2015/0135506 A1 | 5/2015 | White | |
| 2015/0157455 A1 | 6/2015 | Hoang et al. | |
| 2015/0320556 A1* | 11/2015 | Levi | A61F 2/2418 29/515 |
| 2016/0374802 A1 | 12/2016 | Levi et al. | |
| 2017/0014229 A1 | 1/2017 | Nguyen-Thien-Nhon et al. | |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Levi et al. | |
| 2019/0192289 A1 | 6/2019 | Levi et al. | |
| 2019/0209312 A1 | 7/2019 | Zhang et al. | |

FOREIGN PATENT DOCUMENTS

| | | | |
|---|---|---|---|
| DE | 2246526 | A1 | 3/1973 |
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | B1 | 5/1988 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | WO-2012048035 | A2 | 4/2012 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

PROSTHETIC HEART VALVE

CROSS-REFERENCE TO RELATED APPLICATION

This application is a continuation of PCT application no. PCT/US2021/032857 filed May 18, 2021, which application claims the benefit of U.S. Provisional Application No. 63/026,866, filed May 19, 2020, each of these applications being incorporated herein in its entirety by this specific reference.

FIELD

The present disclosure concerns embodiments of a prosthetic valve for implantation into body ducts, such as native heart valve annuluses.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

SUMMARY

Certain embodiments of the disclosure concern a prosthetic valve. The prosthetic valve can include a radially expandable and compressible frame having a plurality of interconnected struts and a valvular structure having a plurality of leaflets configured to regulate the flow of blood through the prosthetic valve. The leaflets can have undulating cusp edge portions. At least one connecting skirt can have a shape that corresponds to the cusp edge portion of at least one leaflet. The connecting skirt can connect the cusp edge portion of the leaflet to at least one of the struts of the frame. The connecting skirt can include a first set of yarns intersecting with a second set of yarns. The first and second sets of yarns can extend at oblique angles relative to a longitudinal axis of the at least one strut.

Certain embodiments of the disclosure also concern a prosthetic valve including a radially expandable and compressible frame having a plurality of interconnected struts. The frame can have an inflow end and an outflow end. The prosthetic valve can also include a valvular structure having a plurality of leaflets configured to regulate the flow of blood through the prosthetic valve. The leaflets can have undulated cusp edge portions. The prosthetic valve can further include a connecting skirt having undulated shape that corresponds to a shape of the cusp edge portions. The connecting skirt can connect the cusp edge portions of the plurality of leaflets to struts of the frame that extend diagonally relative to the inflow and outflow ends of the frame. The connecting skirt can have a first set of yarns interwoven with a second set of yarns. The first set of yarns can extend at an oblique angle relative to the struts connected to the connecting skirt.

Certain embodiments of the disclosure further concern a method for mounting a valvular structure having a plurality of leaflets to a radially expandable and compressible frame. The method can include coupling at least one leaflet to a connecting skirt and coupling the connecting skirt to a strut of the frame that extends diagonally along a line extending from an inflow end of the frame to an outflow end of the frame. The connecting skirt can include a first set of yarns interwoven with a second set of yarns. The connecting skirt can be oriented such that the first set of yarns extend at an oblique angle relative to a longitudinal axis of the strut.

The foregoing and other objects, features, and advantages of the invention will become more apparent from the following detailed description, which proceeds with reference to the accompanying figures.

DETAILED DESCRIPTION

Figure 1A:
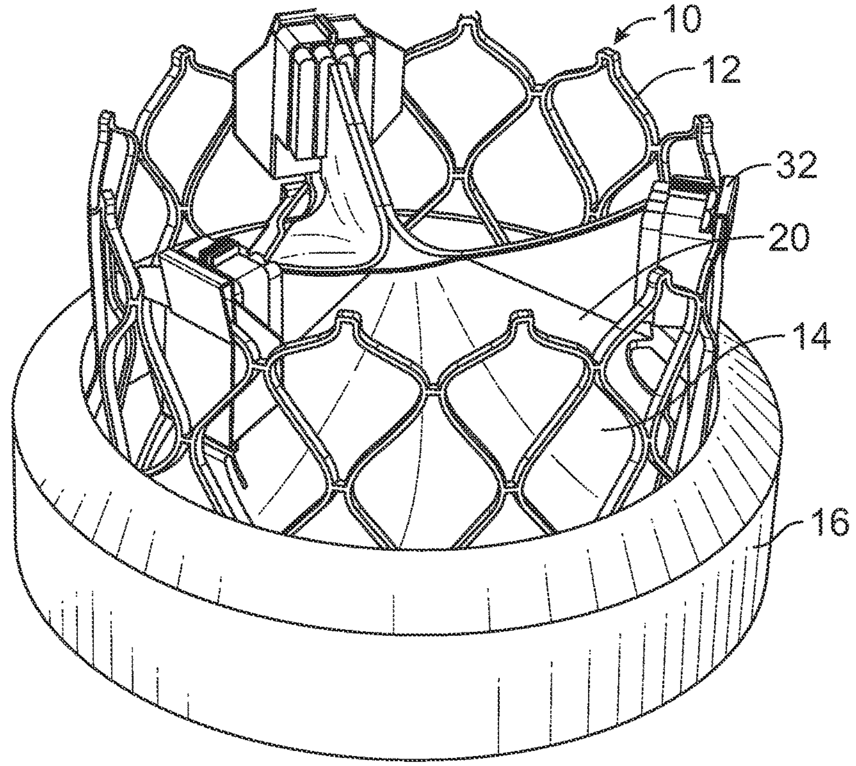
FIG. 1A is a perspective view of a prosthetic heart valve, according to one embodiment.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the prosthetic valves disclosed herein may be used with a variety of implant delivery apparatuses and can be implanted via various delivery procedures, examples of which will be discussed in more detail later.

Any of the prosthetic valves disclosed herein are adapted to be implanted in the native aortic annulus, although in other examples they can be adapted to be implanted in the other native annuluses of the heart (the pulmonary, mitral, and tricuspid valves). The disclosed prosthetic valves also can be implanted within vessels communicating with the heart, including a pulmonary artery (for replacing the function of a diseased pulmonary valve, or the superior vena cava or the inferior vena cava (for replacing the function of a diseased tricuspid valve) or various other veins, arteries and vessels of a patient. The disclosed prosthetic valves also can be implanted within a previously implanted prosthetic valve (which can be a prosthetic surgical valve or a prosthetic transcatheter heart valve) in a valve-in-valve procedure.

In some examples, the disclosed prosthetic valves can be implanted within a docking or anchoring device that is implanted within a native heart valve or a vessel. For example, in one example, the disclosed prosthetic valves can be implanted within a docking device implanted within the pulmonary artery for replacing the function of a diseased pulmonary valve, such as disclosed in U.S. Publication No. 2017/0231756, which is incorporated by reference herein. In another example, the disclosed prosthetic valves can be implanted within a docking device implanted within or at the native mitral valve, such as disclosed in PCT Publication No. WO2020/247907, which is incorporated herein by reference. In another example, the disclosed prosthetic valves can be implanted within a docking device implanted within the superior or inferior vena cava for replacing the function of a diseased tricuspid valve, such as disclosed in U.S. Publication No. 2019/0000615, which is incorporated herein by reference.

The disclosed prosthetic heart valves are particularly suited for implantation in the native aortic valve. In the context of a prosthetic aortic valve, the terms "lower" and "upper" are used interchangeably with the terms "inflow" and "outflow", respectively, for convenience. Thus, for example, the lower end of the prosthetic valve is its inflow end and the upper end of the prosthetic valve is its outflow end in the orientation shown in the drawings. However, it should be understood that the prosthetic valve can be implanted in the reverse orientation. For example, for implantation at the mitral valve position, the upper end of the prosthetic valve is the inflow end and the lower end of the valve is the outflow end.

Figure 1B:
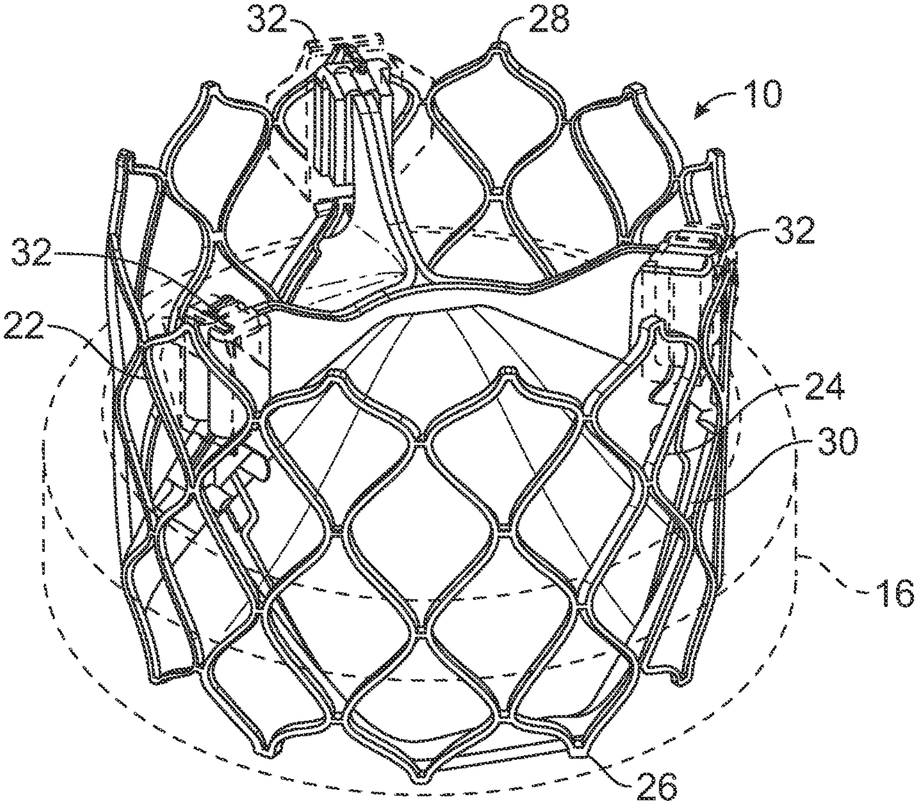
FIG. 1B is a perspective view of the prosthetic heart valve depicted in FIG. 1A, with the components on the outside of the frame shown in transparent lines for purposes of illustration.

FIG. 1A is a perspective view of a prosthetic heart valve 10, according to one embodiment. The illustrated valve is adapted to be implanted in the native aortic annulus, although in other embodiments it can be adapted to be implanted in the other native annuluses of the heart or other locations as described above. The valve 10 can have three main components: a stent, or frame, 12, a valvular structure 14, and a sealing member 16. FIG. 1B is a perspective view of the prosthetic valve 10 with the components on the outside of the frame 12 (including the sealing member 16) shown in transparent lines for purposes of illustration.

Figure 11:
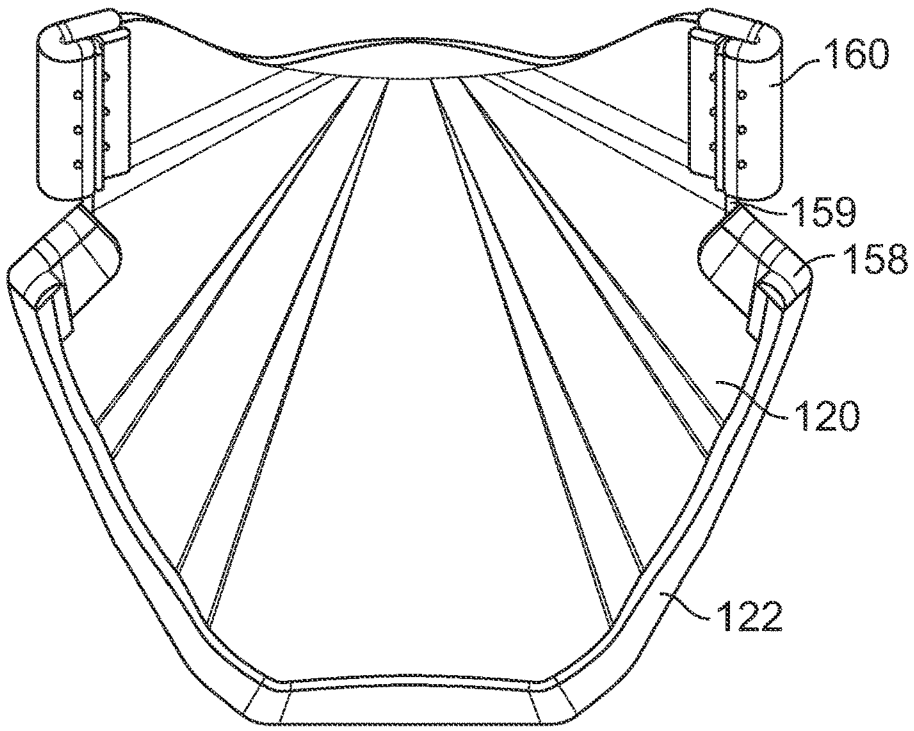
FIG. 11 is a perspective view of a leaflet of the prosthetic heart valve of FIGS. 9-10.

The valvular structure 14 can have three leaflets 20, collectively forming a leaflet structure, which can be arranged to collapse in a tricuspid arrangement, although in other embodiments there can be greater or fewer number of leaflets (e.g., one or more leaflets 20). The lower edge of leaflet structure 14 can have an undulating scalloped shape, which can be a smooth curve or a plurality of U-shape or V-shape undulations with flattened lower central portions (see, e.g., FIGS. 3, 11 and 12). By forming the leaflets with this scalloped geometry, stresses on the leaflets can be reduced, which in turn can improve durability of the valve. Moreover, by virtue of the scalloped shape, folds and ripples at the belly of each leaflet (the central region of each leaflet), which can cause early calcification in those areas, can be eliminated or at least minimized. The scalloped geometry can also reduce the amount of tissue material used to form leaflet structure, thereby allowing a smaller, more even crimped profile at the inflow end of the valve. The leaflets 20 can be formed of pericardial tissue (e.g., bovine or porcine pericardial tissue), biocompatible synthetic materials, or various other suitable natural or synthetic materials as known in the art and described in U.S. Pat. No. 6,730,118, which is incorporated by reference herein.

Each leaflet 20 can be coupled to the frame 12 along its curved inflow edge 30 (the lower edge in the figures; also referred to as "cusp edges") and at commissures 32 of the valvular structure 14 where adjacent portions of two leaflets are connected to each other.

The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the prosthetic valve 10) can be crimped to a radially compressed state on a delivery catheter and then expanded inside a patient by an inflatable balloon or any suitable expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the prosthetic valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

The frame 12 in the illustrated embodiment can include a plurality of circumferentially extending rows of angled struts 22 defining rows of cells, or openings, 24 of the frame. The frame 12 can have a cylindrical or substantially cylindrical shape having a constant diameter from an inflow end 26 to an outflow end 28 of the frame as shown, or the frame can vary in diameter along the height of the frame, as disclosed in U.S. Pat. No. 9,155,619, which is incorporated herein by reference.

The sealing member 16 in the illustrated embodiment is mounted on the outside of the frame 12 and functions to create a seal against the surrounding tissue (e.g., the native leaflets and/or native annulus) to prevent or at least minimize paravalvular leakage. Methods of connecting the sealing member 16 to the frame and alternative embodiments of the sealing member are described in U.S. Patent Publication No. 2018/0028310, which is incorporated herein by reference.

FIGS. 2-6 illustrate a technique for mounting the inflow edges 30 of the leaflets 20 to the frame 12, according to one embodiment.

Figure 3:
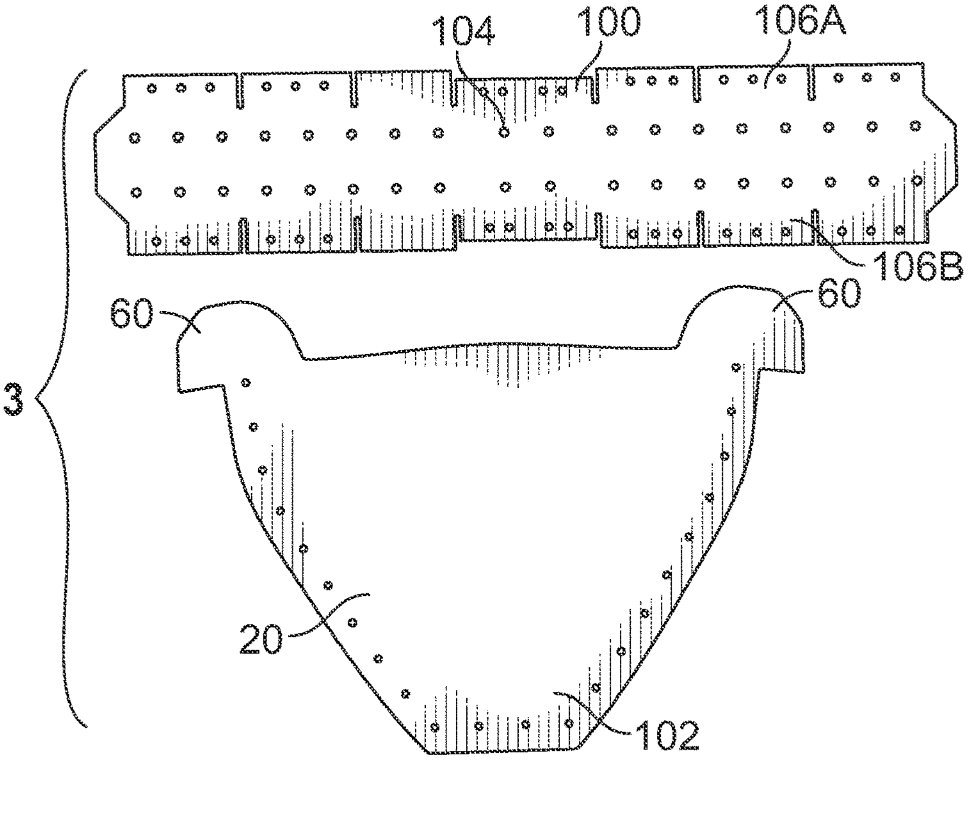
FIG. 3 is a plan view of a leaflet and a connecting skirt used in the prosthetic heart valve of FIG. 2.

In the illustrated embodiment, a connecting skirt 100 is secured to a lower edge portion 102 (also referred to as a cusp edge portion) of each leaflet. As best shown in FIG. 3, each connecting skirt 100 can have an elongated, generally rectangular body 104 formed with a plurality of flaps 106*a*, 106*b* formed along opposing longitudinal edges of the body 104. The skirt 100 can include any suitable synthetic material (e.g., PET) and be woven from yarns, as described more fully below.

As further shown in FIG. 3, each leaflet 20 can have opposing tabs 60. Each tab 60 can be secured to an adjacent tab 60 of an adjacent leaflet 20 to form a commissure 32 that is secured to the frame 12. Methods for mounting commissures to the frame are described in detail in U.S. Patent Publication No. 2018/0028310.

Figure 4:
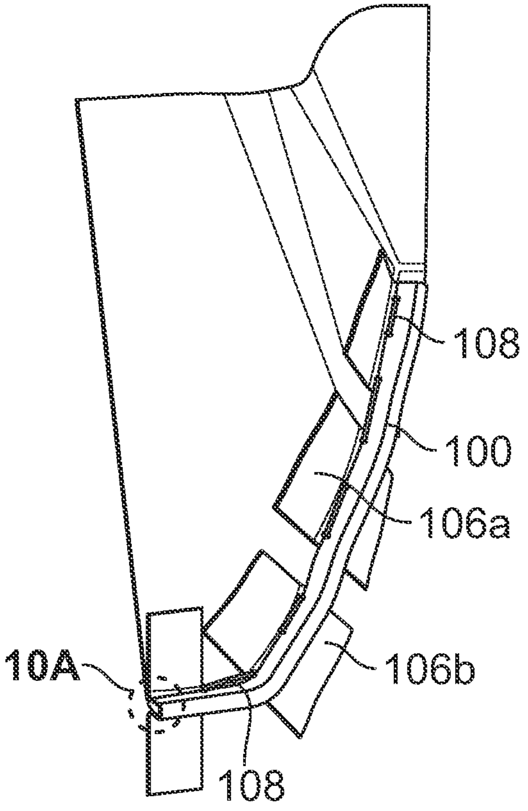
FIG. 4 is a perspective view showing the attachment of a connecting skirt and the leaflet of FIG. 3.
Figure 4A:
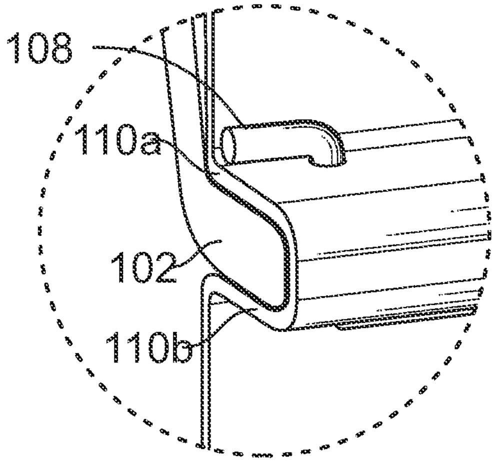
FIG. 4A is an enlarged view of a circled portion depicted in FIG. 4.
Figure 5:
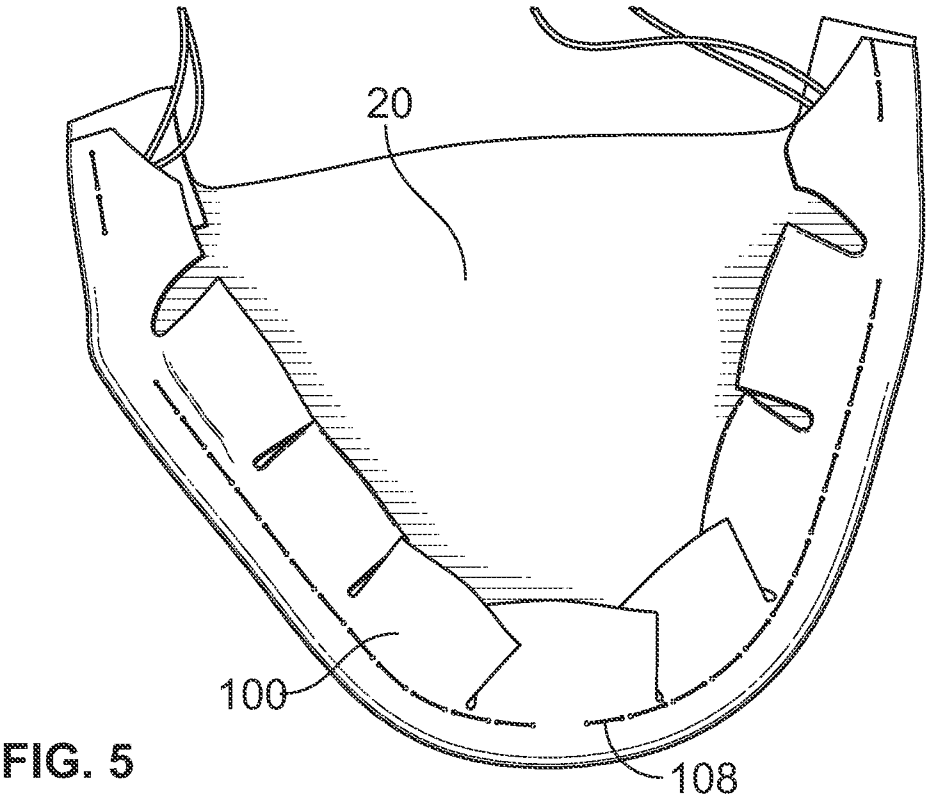
FIG. 5 is a flattened view of a leaflet and a connecting skirt connected thereto.

Referring to FIGS. 4 and 4A, to secure a connecting skirt 100 to a leaflet 20, the body 104 can be folded along a central longitudinal fold bisecting the body to form folded portions 110*a*, 110*b*, which are then placed on opposite sides of the lower edge portion 102 of the leaflet 20 such that the flaps 106*a* are adjacent the outer surface of the leaflet and the flaps 106*b* are adjacent the inner surface of the leaflet. A suture can then be used to form stitches 108 that extend through the opposing portions 110*a*, 110*b* of the body 104 and the lower edge portion 102 of the leaflet and longitudinally along the length of the lower edge portion 102. FIG. 5 shows a flattened view of the leaflet 20 with the skirt 100 folded around the lower edge portion 102 of the leaflet and secured thereto with stitches 108. As shown, the shape of the connecting skirt 100 generally corresponds to the curved cusp edge portion 102 of the leaflet 20.

Figure 6:
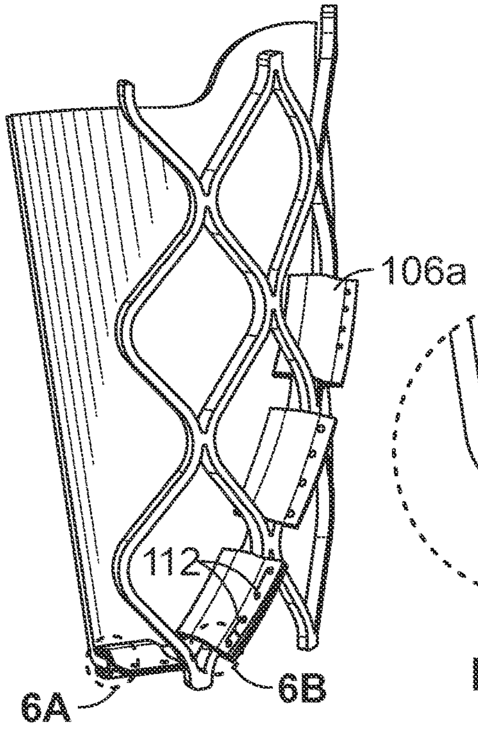
FIG. 6 is a perspective view showing the connection of the connecting skirt of FIG. 3 to the frame of the prosthetic heart valve of FIG. 2.
Figure 6A:
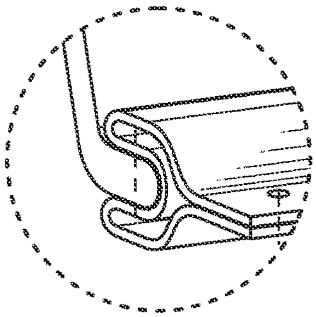
FIG. 6A is an enlarged view of a circled portion depicted in FIG. 6.
Figure 6B:
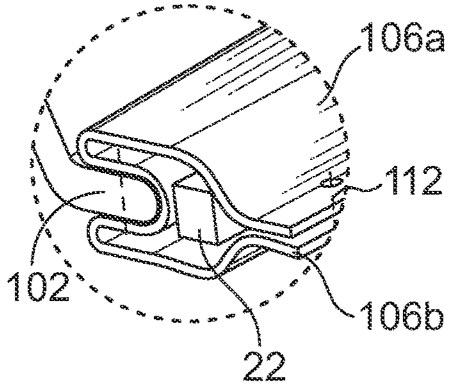
FIG. 6B is an enlarged view of another circled portion depicted in FIG. 6.

Referring to FIGS. 6, 6A, and 6B, each pair of flaps 106*a*, 106*b* can be folded away from the leaflet 20 over a respective strut 22 of the frame and secured in place with stitches 112 that extend through the flaps 106*a*, 106*b* along a stitching line outside of the frame 12. As best shown in FIG. 6B, the connecting skirt 100 can mount the leaflet to the frame 12 such that the lower edge portion 102 extends radially inwardly at about a 90-degree angle relative to the frame 12. This effectively moves the bending axis of the lower edge portion 102 inwardly away from the inner surface of the frame and toward the center of the frame.

Figure 2:
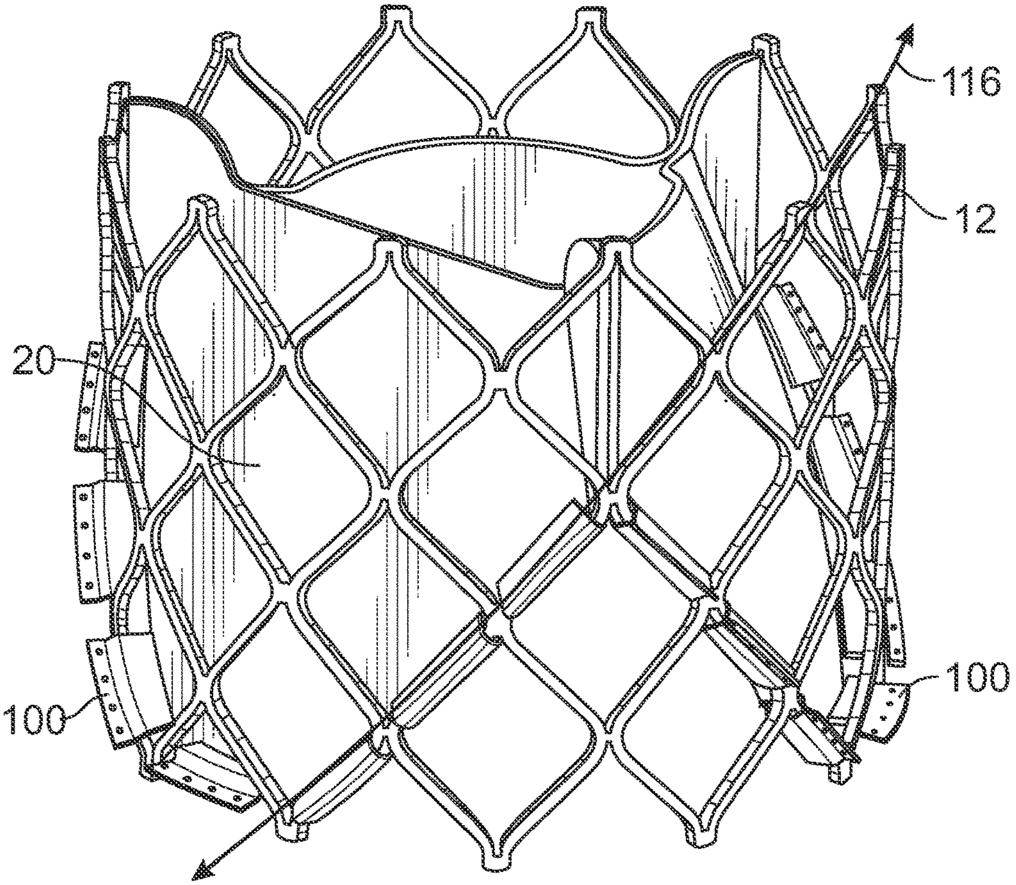
FIG. 2 is a perspective view of a partially assembled prosthetic heart valve showing the attachment of leaflets using connecting skirts, according to one embodiment.

As best shown in FIG. 2, each of the skirts 100 can be secured to the frame along a diagonal line 116 extending along the curved surface of the frame defined by a diagonally extending row of struts 22 extending from the inflow end of the frame toward the outflow end. In other words, the longitudinal axis of each strut 22 connecting the respective skirt 100 extends at an oblique angle relative to a central longitudinal axis of the frame. As such, the lower edge portion 102 of each leaflet can also be positioned along a respective diagonal line 116 defined by a respective diagonally extending row of struts 22. This can advantageously reduce tension and the formation of wrinkles in the leaflets 20.

The attachment along diagonal lines 116 can also help reduce the crimping profile of the prosthetic valve when the prosthetic valve is radially compressed to its delivery configuration. In particular, struts in a circumferentially extending row of struts of the frame are moved or bent toward each other during the crimping process while struts lying along diagonally extending lines 116 substantially retain their alignment relative to each other along lines 116 during the crimping process. As such, the connecting skirts 100 (which typically are formed from non-stretchable materials) do not inhibit movement or deformation of the struts relative to each other. Also, since the cusp edge portions of the leaflets move with the connecting skirts during crimping, stretching of the leaflets along the cusp edge portions is prevented or at least minimized.

Further, the connecting skirts 100 (and the other connecting skirts described herein) can facilitate assembly of the prosthetic valve compared to known assembly techniques. For example, the leaflets and the skirts can be assembled while the leaflets are in a flattened configuration, prior to forming the tubular (annular) configuration the valvular structure 14. Automated or semi-automated techniques can be used to suture the skirts to the leaflets. Also, once the valvular structure is placed inside of the frame, the lower edge portions 102 of the leaflets can be secured to the frame with stitching that is completely outside of the frame 12. This can substantially reduce assembly time as the assembler does not have to thread the needle for forming stitches 112 in and out of the cells 24 of the frame. Moreover, as described below, the woven yarns of the connecting skirt 100 can be configured to extend at oblique angles relative to struts connected to the connecting skirt 100 so as to improve the durability of the connecting skirt 100.

Figure 7:
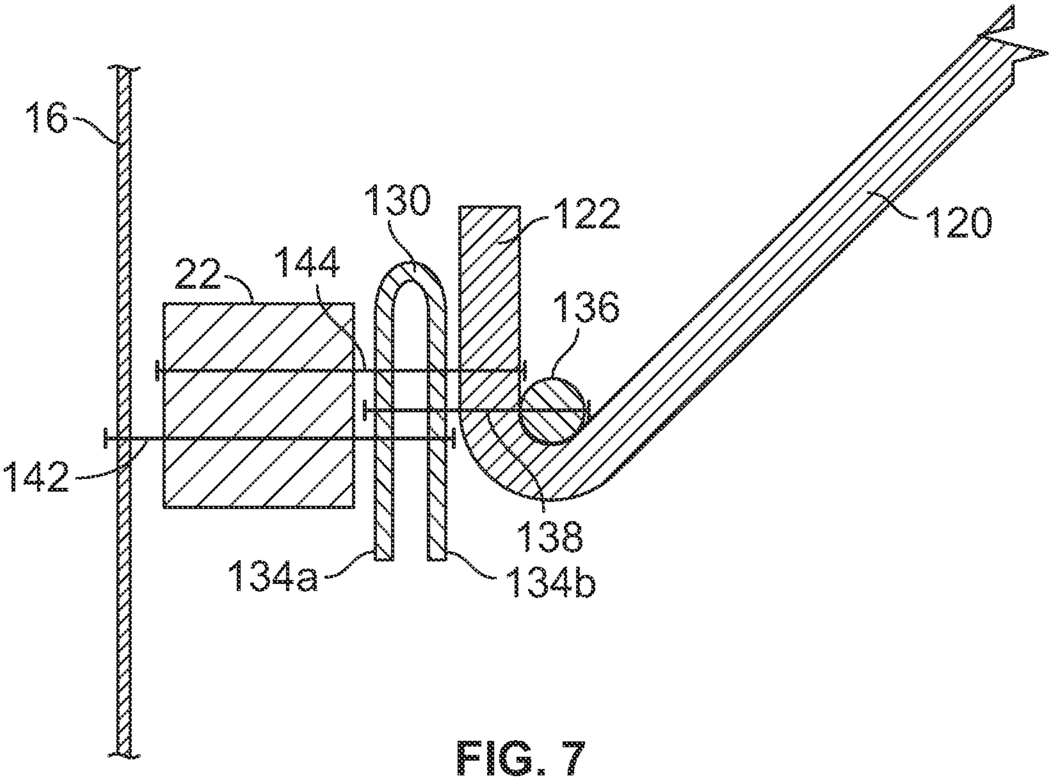
FIG. 7 is a cross-sectional view showing the attachment of a cusp edge portion of a leaflet to a connecting skirt, according to another embodiment.
Figure 9:
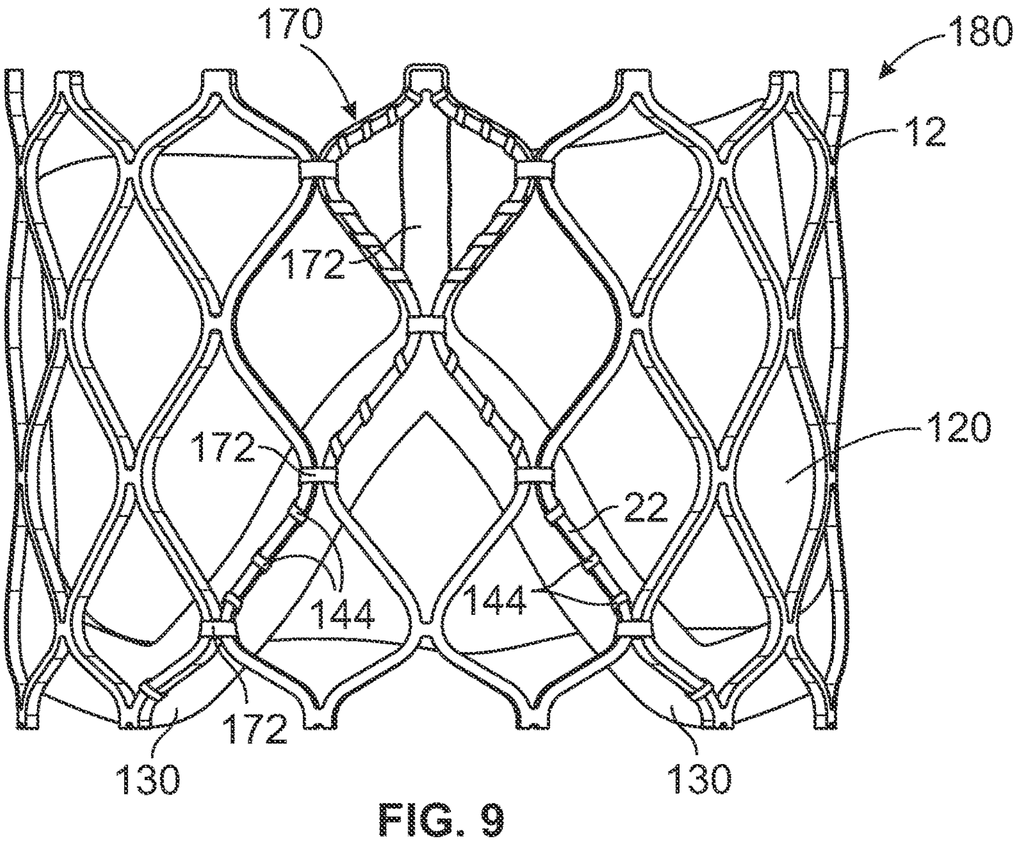
FIG. 9 is a side elevation view of a prosthetic heart valve including a frame and a valve assembly mounted inside the frame, according to one embodiment.

FIG. 9 shows a prosthetic valve 180, according to another embodiment. The prosthetic valve 180 can include leaflets 120 connected to each other at their outflow ends to form commissures 170 that are mounted to the cells at the outflow end of the frame. The commissures 170 can be formed by folding commissure tabs of the leaflets and securing them to a commissure attachment member 172. Each commissure attachment member 172 can be sutured to four struts 22 that define a closed cell 24 of the frame. The method for forming the commissures 170 and mounting them to a cell 24 via the commissure attachment members 172 is described in detail in U.S. Patent Publication No. 2018/0028310. As shown in FIG. 7, the prosthetic valve 180 can also include a sealing member 16 mounted to the outside of the frame 12 (the sealing member is omitted from FIG. 9 for clarity).

Figure 12:
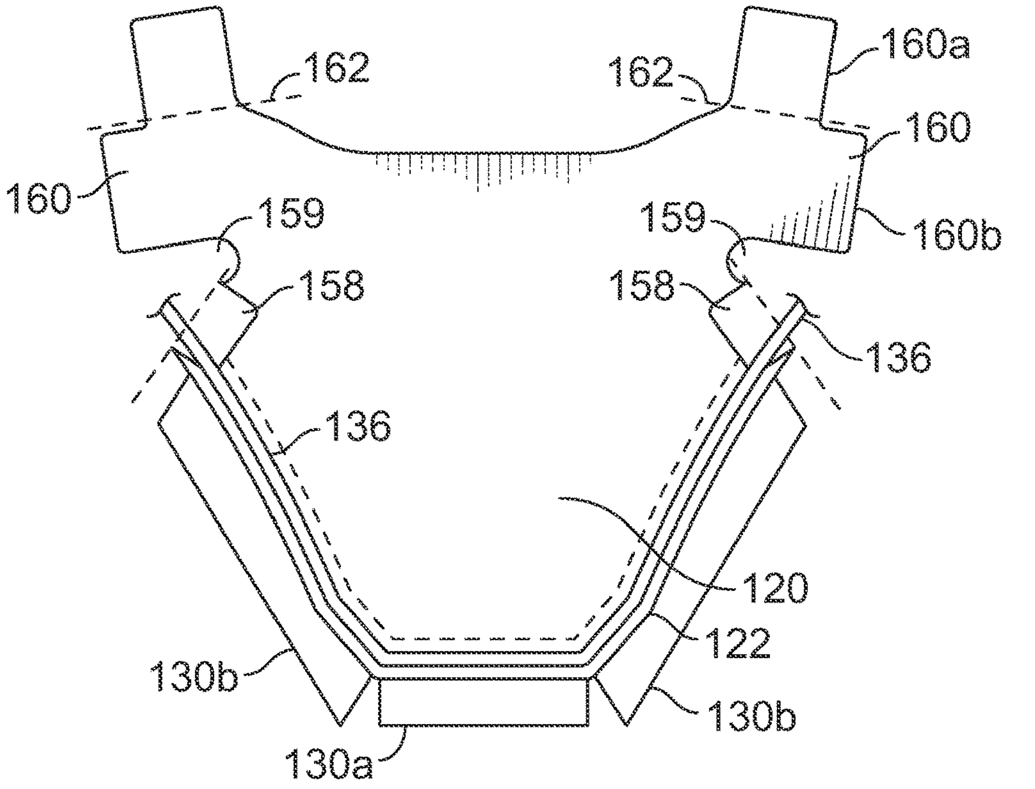
FIG. 12 is a plan view of the leaflet of FIG. 11 and the connecting skirt of FIG. 8 positioned along the cusp edge portion of the leaflet.

As best shown in FIG. 12, each leaflet 120 has a lower or cusp edge portion 122 that can be mounted to the frame 12. The cusp edge portion 122 in the illustrated embodiment has a generally U shape with a flattened lower central portion with side portions extending upwardly from the central portion toward lower tabs 158. The lower edge portion 122 can terminate at its upper ends at two laterally projecting integral lower tabs 158. Projecting from the upper corners of the leaflet 120 are integral upper tabs 160 (also referred to as commissure tabs). The upper tabs 160 can be spaced from the lower tabs 158 by side edges 159 forming laterally extending gaps or recesses 160 in the leaflet. Each upper tab 160 can be folded along a fold line 162 to form first and second tab layers 160*a*, 160*b*. The upper tab 160 can be secured to a commissure attachment member 172, along with the upper tab 160 of an adjacent leaflet to form a commissure 170.

Figure 8:
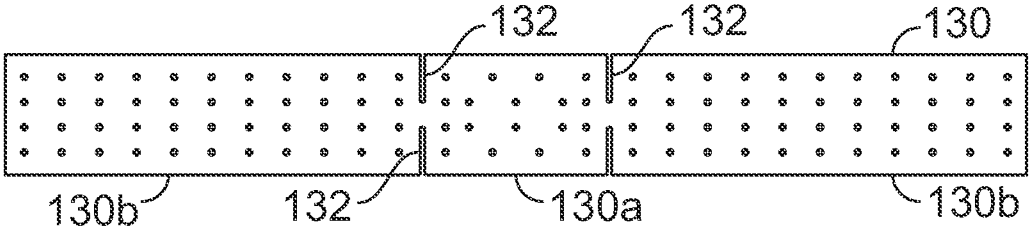
FIG. 8 is a plan view of an embodiment of the connecting skirt of FIG. 7, shown in the flattened configuration.

The inflow or cusp edge portions 122 of the leaflets 120 can be secured to the frame 12 using a plurality of connecting skirts 130 (FIG. 8), which can be formed of the same materials as described above for the connecting skirt 100 (e.g., PET fabric). In the illustrated embodiment, a single connecting skirt 130 is provided for the cusp edge portion 122 of each leaflet 120. The connecting skirt 130 can have a shape that corresponds to the curved cusp edge portion 122, and be sized to extend along the entire length of the cusp edge portion 122 to locations just below the lower tabs 158 of the leaflet 120. FIG. 12 shows a connecting skirt 130 placed along the cusp edge portion 122 of a leaflet 120 prior to being attached to the leaflet with sutures. The connecting skirt 130 can include a central portion 130*a* sized to extend over the central lower edge portion and two side portions 130*b* sized to extend over the angled side edge portions extending from the lower central portion to the lower tabs 158. The connecting skirt 130 can be formed with slits 132 partially separating the side portions 130*b* from the central portion 130*a* to facilitate alignment of the skirt along the cusp edge portion as shown in FIG. 12. In alternative embodiments, the connecting skirt 130 can be curved to match the curvature of the cusp edge 122 of the leaflet.

In alternative embodiments, plural connecting skirts can be provided for the cusp edge portion of each leaflet (e.g., the central portion 130*a* and the side portions 130*b* can be separate pieces of fabric). In another embodiment, a single connecting skirt can be used to secure all of the leaflets to the frame; i.e., a single connecting skirt can be sized to extend along the cusp edge portions of all of the leaflets. For example, the single connecting skirt can include a plurality of skirt segments, each skirt segment connecting a corresponding cusp edge portion of a leaflet to a respective strut (or struts). The cusp edge portions of the leaflets can form an undulated shape or curvature. The single connecting skirt can have undulated shape that corresponds to a curvature of the cusp edge portions of the leaflets.

Prior to attaching the leaflets to the frame, a connecting skirt 130 can be attached to the cusp edge portion of each leaflet. As shown in FIG. 7, a connecting skirt 130 can be folded lengthwise to form two fold layers 134*a*, 134*b* and placed against the inflow surface of the cusp edge portion 122. Optionally, a reinforcing member or chord 136 (e.g., an Ethibond suture) can be placed against the outflow surface of the cusp edge portion opposite the connecting skirt 130. The reinforcing member 136 and the fold layers 134*a*, 134*b* can be sutured to each other and to the cusp edge portion 122 with stitching 138, which can be a single suture or multiple sutures extending through one or more layers of material.

When suturing the reinforcing chord 136 to the leaflet 120, the lower tabs 158 can be folded downwardly against the cusp edge portion 122 (see FIG. 12) and the reinforcing chord 136 can be placed over the folded lower tab 158. The upper ends of the connecting skirt 130 can be sized to extend over the folded lower tabs 158. Stitching 138 can be used to secure the reinforcing chord 136 in place against the folded lower tab 158. In particular embodiments, the reinforcing chord 136 can extend along the folded lower tab 158 of one leaflet 120, through the space between a pair of adjacent lower tabs 158 and a pair of upper tabs 160 under a commissure 170, and then along the lower tab 158 and the cusp edge portion of the adjacent leaflet 120. In some embodiments, a single reinforcing chord 136 can extend continuously along the cusp edge portions 122 of all of the leaflets and through the spaces beneath each commissure 170. In other embodiments, plural reinforcing chords 136 can be used, with one reinforcing chord secured to the cusp edge portion of each leaflet. Where multiple reinforcing chords 136 are used, the ends of each chord can be connected (e.g., by tying or knotting) to adjacent ends of the other chords. For example, adjacent ends of two chords can be connected to each in the space underneath a commissure.

Figure 10:
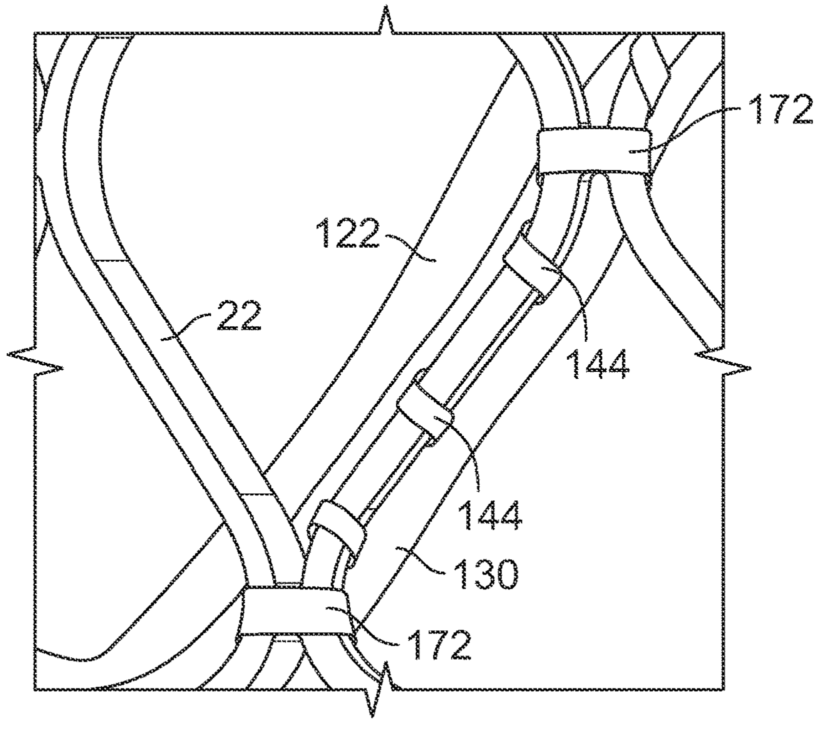
FIG. 10 is an enlarged view of a portion of the frame and the valve assembly of FIG. 9.

FIGS. 7, 9 and 10 illustrate the connection of the connecting skirts 130 to the frame 12, according to one embodiment. As shown, the connecting skirt 130 can be sutured to struts 22 of the frame 12 forming a diagonal line extending from a commissure 170 to the inflow end of the frame. In particular embodiments, one or both layers 134*a*, 134*b* of the connecting skirt can be secured to junctions 128 (formed by the intersection of struts 22) by individual stitches 172, and further with whip stitches 144 that are formed along the length of a strut 22 between two junctions 128. Each whip stitch 144 can extend through an edge portion 142 and around a strut 22 multiple times along the length of the strut. The whip stitches 144 optionally can extend through the cusp edge portion 122, as depicted in FIG. 7. Further, as described below, the yarns of the connecting skirt 130 can be configured to extend at oblique angles relative to the connecting struts 22 so as to improve the durability of the connecting skirt 130.

As disclosed herein, the folded lower tabs 158 help reinforce the connection between the cusp edge portions 122 of the leaflets and the frame along the upper sections of the cusp edge portions adjacent the commissures 170. The folded lower tabs 304 can also move the bending axes of the upper sections of the cusp edge portions inwardly and away from the inner surface of the frame to prevent or minimize contact between the leaflets and the frame in the areas below the commissures. In the illustrated embodiment, each lower tab 158 forms one additional layer of leaflet material on the upper (outflow) surface of the leaflet. In alternative embodiments, each lower tab 158 can be configured to form multiple additional layers of leaflet material, such as two, three, or four layers, on the upper surface of the leaflet to move the bending axes of the leaflet below the commissures even further away from the inner surface of the frame.

The side edges 159 between the lower and upper tabs 158, 160 can be left unattached to the frame of the prosthetic valve. The unattached side edges 159 can allow greater elongation or stretching of the leaflets in the axial direction when the prosthetic valve is compressed and allowing greater elongation or stretching of the leaflets in the radial direction when the prosthetic valve is expanded. During diastole, the adjacent side edges 159 can coapt with each other and prevent retrograde blood from flowing between the side edges 159. During systole, the adjacent side edges 159 can separate from each other and allow antegrade blood to flow between side edges 159 and help wash away blood from the areas underneath the commissures 170.

Figure 13:
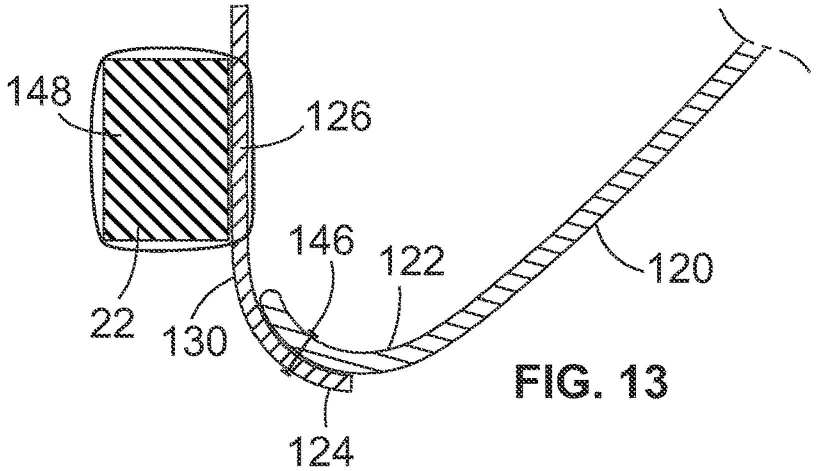
FIG. 13 is a cross-section view showing the coupling a leaflet to a strut of the frame using a connecting skirt, according to another embodiment.

FIG. 13 schematically illustrates connection of the connecting skirt 130 to an adjacent strut 22, according to another embodiment. As shown, a first longitudinal edge portion 124 of the connecting skirt 130 is coupled to the cusp edge portion 122 of the leaflet 120. A second longitudinal edge portion 126 of the connecting skirt 130 is coupled to an adjacent strut 22. The second edge portion 126 is opposite the first edge portion 124.

The first edge portion 124 of the connecting skirt 130 can extend along an entire length of the cusp edge portion 122 of the leaflet 120, similar to the embodiment shown in FIG. 12. The first edge portion 124 of the connecting skirt 130 and the cusp edge portion 122 of the leaflet 120 can be are coupled together by one or more stitches 146. Optionally, a reinforcing chord (not shown) can be placed against the outflow surface of the cusp edge portion opposite the first longitudinal edge portion 124 of the connecting skirt 130, similar to the example shown in FIG. 7. The reinforcing cord can be coupled together to the cusp edge portion 122 and the first edge portion 124 by the stitches 146.

As shown in FIG. 13, the second edge portion 126 of the connecting skirt 130 can be attached to the frame with one or more sutures 148. Each suture 148 can extend around the connecting strut 22 and through the skirt 130 at one or more locations so as to form one or more loops around the strut 22. For example, each suture 148 can be used to form a plurality of whip stitches that extend around the strut 22 and the through the skirt 130.

Figure 14:
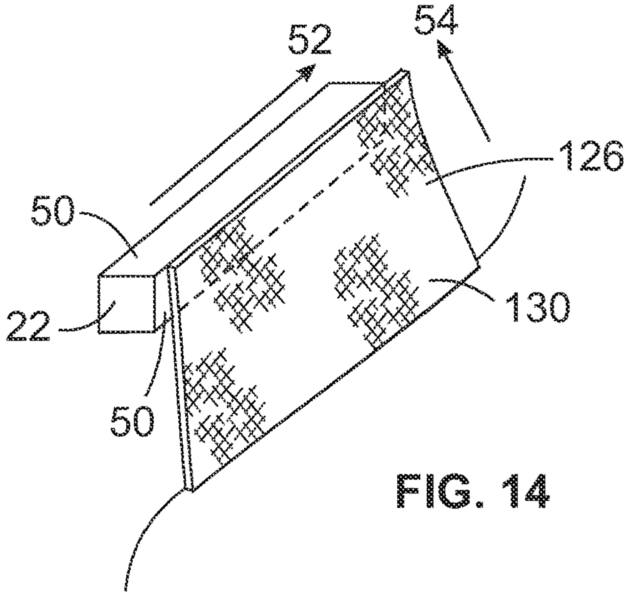
FIG. 14 is a schematic view showing an edge portion of the connecting skirt overlaying a portion of an outer surface of a strut, according to one embodiment.

The second edge portion 126 of the connecting skirt 130 in the illustrated embodiment is configured to overlay at least a portion of an inner surface of the connecting strut 22. For example, as illustrated in FIG. 14, the strut 22 is shown to have a quadrangular cross-section and four sides 50, and the second edge portion 126 of the connecting skirt 130 overlays only one of the four sides 50. The arrow 52 denotes a direction parallel to the longitudinal axis of the strut 22, and the arrow 54 denotes a direction that is substantially perpendicular or transverse to direction 52. In other embodiments, the cross-section of the strut 22 can have a non-quadrangular shape and thus the strut can have any number of sides. In alternative embodiments, the second edge portion 126 of the connecting skirt 130 can overlay at least two of the sides of the strut.

Although FIGS. 13-14 show the connecting skirt 130 coupled to the strut 22 as an example, similar coupling mechanism can be applied to the connecting skirt 100 described above. For example, the skirt 130 can have a plurality of flaps that extend at least partially around the strut 22. In a specific implementation, the skirt 130 can have a plurality of flaps **106*a* and a plurality of flaps 106*b*, wherein the flaps 106*a*, and 106*b* can be connected to the strut 22 in the manner shown in FIGS. 2, 6, 6A, and 6B. In another embodiment, the skirt 130 can be folded and attached to a strut 22 in the manner shown in FIG. 7**.

Figure 15:
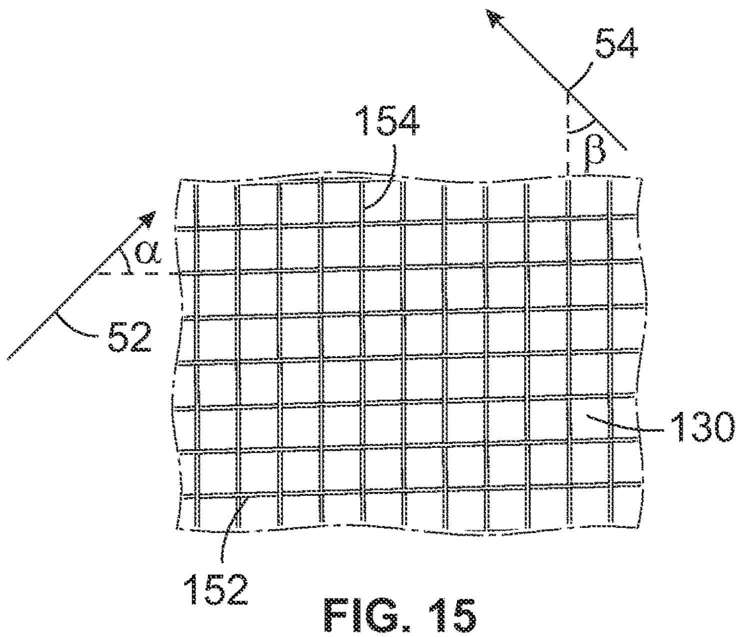
FIG. 15 is a schematic view of orientation of the yarns in a connecting skirt relative to a connecting strut, according to one embodiment.

FIG. 15 shows a portion of the yarns of a connecting skirt 130 (or 100), according to one embodiment. As shown, the connecting skirt 130 includes a first set of yarns 152 intersecting with a second set of yarns 154. The yarns 152, 154 can be made of natural or synthetic materials. Each yarn 152 or 154 can be a monofilament (e.g., a single fiber) or a multi-filament fiber or strand. The first set of yarns 152 can be perpendicular to the second set of yarns 154. In some embodiments, the first set of yarns 152 are woven with the second set of yarns 154. In alternative embodiments, the connecting skirt 130 can have a knitted or braided structure rather than the woven structure.

Similarly, FIG. 15 shows two arrows 52, 54 respectively denoting the longitudinal and transverse directions of an adjacent strut 22 to which the connecting skirt 130 is coupled. As shown, when the connecting skirt 130 is coupled to the adjacent strut 22, the first set of yarns 152 can extend at an oblique angle ($\alpha$) relative to the longitudinal direction (as indicated by arrow 52) of the connecting strut 22. Similarly, the second set of yarns 154 can extend at an oblique angle ($\beta$) relative to the transverse direction (as indicated by arrow 54) of the connecting strut 22. In particular embodiments, the angle $\alpha$ (or $\beta$) can range between about 20 and 70 degrees in some examples; more desirably between about 30 and 60 degrees in some examples; and even more desirably between about 40 and 50 degrees in some examples. In a specific embodiment, the angle $\alpha$ (or $\beta$) is about 45 degrees.

Conventionally, the interwoven yarns of the connecting skirt are either parallel or perpendicular to the longitudinal axis of the connecting struts. Cyclic movements of the leaflets can cause abrasion of the connecting skirt against the connecting struts. The angled orientation of the interwoven yarns relative to the connecting strut described above can advantageously provide a larger overlap or contacting area between the yarns and the struts, which in turn can result in improved durability of the connecting skirts over time.

Delivery Apparatus

Figure 16:
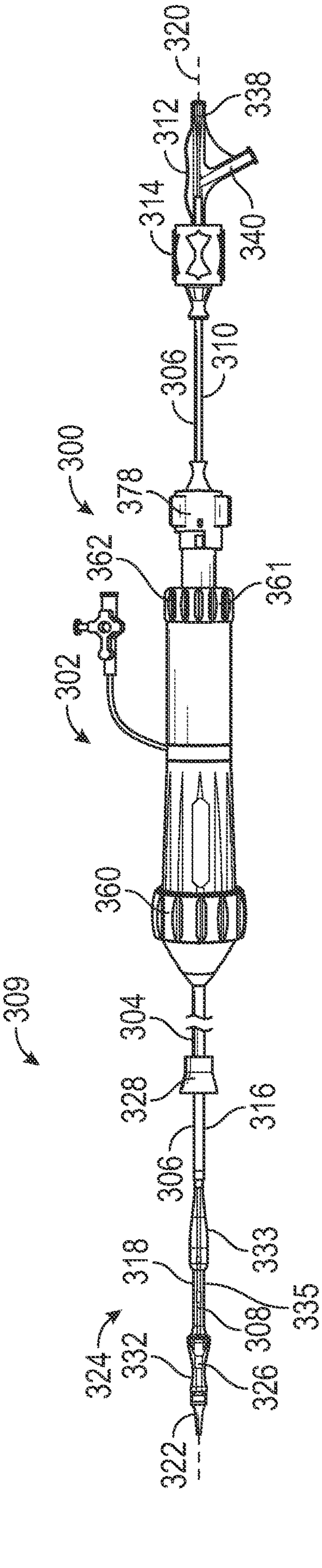
FIG. 16 is a side view of an embodiment of a delivery apparatus configured to deliver and implant a radially expandable prosthetic heart valve at an implantation site.
Figure 17:
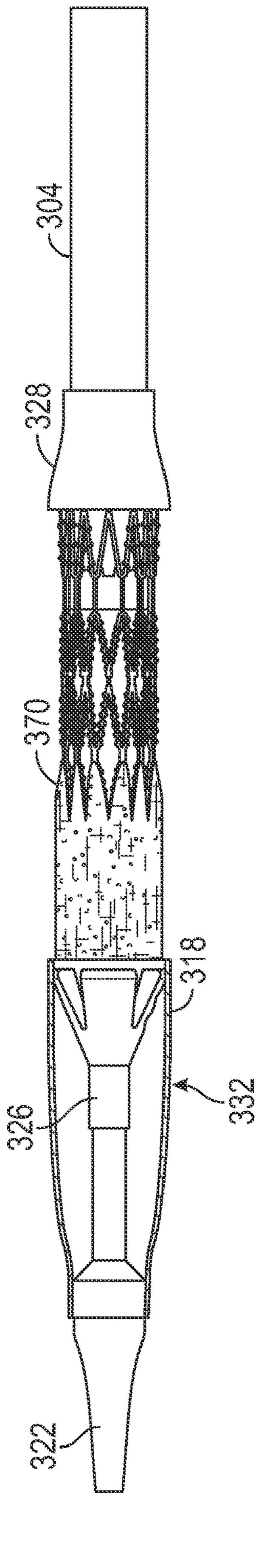
FIG. 17 is a side view of the distal end portion of the delivery apparatus of FIG. 16 with a prosthetic heart valve mounted on a valve mounting portion of the delivery apparatus.

FIGS. 16 and 17 show a delivery apparatus 300, according to an embodiment, that can be used to implant an expandable prosthetic heart valve (e.g., prosthetic valve 10 of FIGS. 1A and 1B and/or prosthetic heart valve 180 of FIG. 9), or another type of expandable prosthetic medical device (such as a stent). In some embodiments, the delivery apparatus 300 is specifically adapted for use in introducing a prosthetic valve into a heart.

The delivery apparatus 300 in the illustrated embodiment of FIGS. 16 and 17 is a balloon catheter comprising a handle 302 and a steerable, outer shaft 304 extending distally from the handle 302 (FIG. 16). The delivery apparatus 300 can further comprise an intermediate shaft 306 (which can also be referred to as a balloon shaft) that extends proximally from the handle 302 (FIG. 16) and distally from the handle 302, the portion extending distally from the handle 302 also extending coaxially through the outer shaft 304. Additionally, the delivery apparatus 300 can further comprise an inner shaft 308 extending distally from the handle 302 coaxially through the intermediate shaft 306 and the outer shaft 304 (FIG. 16) and proximally from the handle 302 coaxially through the intermediate shaft 306.

The outer shaft 304 and the intermediate shaft 306 can be configured to translate (e.g., move) longitudinally, along a central longitudinal axis 320 of the delivery apparatus 300, relative to one another to facilitate delivery and positioning of a prosthetic valve at an implantation site in a patient's body.

The intermediate shaft 306 can include a proximal end portion 310 that extends proximally from a proximal end of the handle 302, to an adaptor 312 (FIG. 16). In some embodiments, a rotatable knob 314 can be mounted on the proximal end portion 310 (FIG. 16) and can be configured to rotate the intermediate shaft 306 around the central longitudinal axis 320 of the delivery apparatus 300 and relative to the outer shaft 304.

The adaptor 312 can include a first port 338 configured to receive a guidewire therethrough and a second port 340 configured to receive fluid (e.g., inflation fluid) from a fluid source. The second port 340 can be fluidly coupled to an inner lumen of the intermediate shaft 306.

The intermediate shaft 306 can further include a distal end portion 316 that extends distally beyond a distal end of the outer shaft 304 (FIG. 16) when a distal end of the outer shaft 304 is positioned away from an inflatable balloon 318 of the delivery apparatus. A distal end portion of the inner shaft 308 can extend distally beyond the distal end portion 316 of the intermediate shaft 306 (FIG. 16).

The balloon 318 can be coupled to the distal end portion 316 of the intermediate shaft 306. For example, in some embodiments, a proximal end portion of the balloon 318 can be coupled to and/or around a distal end of the intermediate shaft 306 (FIG. 16).

The balloon 318 can comprise a distal end portion (or section) 332, a proximal end portion (or section) 333, and an intermediate portion (or section) 335, the intermediate portion 335 disposed between the distal end portion 332 and the proximal end portion 333 (FIG. 16).

In some embodiments, a distal end of the distal end portion 332 of the balloon 318 can be coupled to a distal end of the delivery apparatus 300, such as to a nose cone 322 (as shown in FIGS. 16 and 17), or to an alternate component at the distal end of the delivery apparatus 300 (e.g., a distal shoulder). In some embodiments, the intermediate portion 335 of the balloon 318 can overlay a valve mounting portion 324 of a distal end portion 309 of the delivery apparatus 300, the distal end portion 332 can overly a distal shoulder 326 of the delivery apparatus 300, and the proximal end portion 333 can surround a portion of the inner shaft 308. The valve mounting portion 324 and the intermediate portion 335 of the balloon 318 can be configured to receive a prosthetic heart valve 370 in a radially compressed state, as shown in FIG. 17. In some embodiments, the prosthetic heart valve 370 shown in FIG. 17 can be one of valve 10 of FIGS. 1A and 1B or valve 180 of FIG. 9.

In some embodiments, rotation of the intermediate shaft 306 can result in rotation of the balloon 318 and the prosthetic valve mounted thereon for rotational positioning of the prosthetic valve relative to the native anatomy at the target implantation site.

The balloon shoulder assembly is configured to maintain the prosthetic heart valve or other medical device at a fixed position on the balloon 318 during delivery through the patient's vasculature. The balloon shoulder assembly can include a distal shoulder 326 (FIGS. 16 and 17) arranged within the distal end portion 332 of the balloon 318 and coupled to the distal end portion of the inner shaft 308. The distal shoulder 326 can be configured to resist movement of the prosthetic valve or other medical device mounted on the valve mounting portion 324 distally, in an axial direction (e.g., along central longitudinal axis 320), relative to the balloon 318.

The outer shaft 304 can include a distal tip portion 328 mounted on its distal end (FIGS. 16 and 17). The outer shaft 304 and the intermediate shaft 306 can be translated axially relative to one another to position the distal tip portion 328 adjacent to a proximal end of the valve mounting portion 324, when a prosthetic valve is mounted in the radially compressed state on the valve mounting portion 324 and during delivery of the prosthetic valve to the target implantation site (as shown in FIG. 17). As such, the distal tip portion 328 can be configured to resist movement of the prosthetic valve relative to the balloon 318 proximally, in the axial direction, relative to the balloon 318, when the distal tip portion 328 is arranged adjacent to a proximal side of the valve mounting portion 324 (FIG. 17).

In some embodiments, the nose cone 322 can be disposed distal to and be coupled to the distal shoulder 326. In some embodiments, the nose cone 322 can be coupled to the distal end portion of the inner shaft 308.

In some embodiments, an annular space can be defined between an outer surface of the inner shaft 308 and an inner surface of the intermediate shaft 306. In some embodiments, the annular space can be referred to as an inner lumen of the intermediate shaft 306. In some embodiments, the annular space can be configured to receive fluid from a fluid source via the second port 340 of the adaptor 312 (e.g., the annular space is in fluid communication with the second port 340 of the adaptor 312). The annular space can be fluidly coupled to a fluid passageway formed between the outer surface of the distal end portion of the inner shaft 308 and an inner surface of the balloon 318. As such, fluid from the fluid source can flow to the balloon 318 to inflate the balloon 318 and radially expand and deploy the prosthetic valve (e.g., prosthetic valve 370 shown in FIG. 17).

An inner lumen of the inner shaft 308 can be configured to receive a guidewire therethrough, for navigating the distal end portion 309 of the delivery apparatus 300 to the target implantation site. As introduced above, the first port 338 of the adaptor 312 can be coupled to the inner lumen and configured to receive the guidewire. For example, the distal end portion 309 of the delivery apparatus 300 can be advanced over the guidewire, to the target implantation site.

As shown in FIG. 16, the handle 302 can include a steering mechanism configured to adjust the curvature of the distal end portion 309 of the delivery apparatus 300. In the illustrated embodiment, for example, the handle 302 includes an adjustment member, such as the illustrated rotatable knob 360, which in turn is operatively coupled to the proximal end portion of a pull wire. The pull wire can extend distally from the handle 302 through the outer shaft 304 and has a distal end portion affixed to the outer shaft 304 at or near the distal end of the outer shaft 304. Rotating the knob 360 can increase or decrease the tension in the pull wire, thereby adjusting the curvature of the distal end portion 309 of the delivery apparatus 300. Further details on steering or flex mechanisms for the delivery apparatus can be found in U.S. Pat. No. 9,339,384, which is incorporated by reference herein.

The handle 302 can include one or more additional adjustment mechanisms. For example, in some embodiments, the handle 302 can include an adjustment mechanism 361 including an adjustment member, such as the illustrated rotatable knob 362. The adjustment mechanism 361 can be configured to adjust the axial position of the intermediate shaft 306 relative to the outer shaft 304. In some embodiments, the handle 302 can further include a locking mechanism, which can include a rotatable knob 379, the locking mechanism configured to retain (e.g., lock) the position of the intermediate shaft 306 relative to the handle 302 and allow for fine positioning of the prosthetic valve 370 at the implantation site.

Further details regarding the delivery apparatus 300 are disclosed in U.S. Provisional Application No. 63/138,890, filed Jan. 19, 2021, which is incorporated herein by reference.

Delivery Techniques

For implanting a prosthetic valve (e.g., valve 10 or 180) within the native aortic valve via a transfemoral delivery approach, the prosthetic valve is mounted in a radially compressed state along the distal end portion of a delivery apparatus (e.g., delivery apparatus 300). The prosthetic valve and the distal end portion of the delivery apparatus are inserted into a femoral artery and are advanced into and through the descending aorta, around the aortic arch, and through the ascending aorta. The prosthetic valve is positioned within the native aortic valve and radially expanded (e.g., by inflating a balloon, actuating one or more actuators of the delivery apparatus, or deploying the prosthetic valve from a sheath to allow the prosthetic valve to self-expand). Alternatively, a prosthetic valve can be implanted within the native aortic valve in a transapical procedure, whereby the prosthetic valve (on the distal end portion of the delivery apparatus) is introduced into the left ventricle through a surgical opening in the chest and the apex of the heart and the prosthetic valve is positioned within the native aortic valve. Alternatively, in a transaortic procedure, a prosthetic valve (on the distal end portion of the delivery apparatus) are introduced into the aorta through a surgical incision in the ascending aorta, such as through a partial J-sternotomy or right parasternal mini-thoracotomy, and then advanced through the ascending aorta toward the native aortic valve.

For implanting a prosthetic valve within the native mitral valve via a transseptal delivery approach, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, into the right atrium, across the atrial septum (through a puncture made in the atrial septum), into the left atrium, and toward the native mitral valve. Alternatively, a prosthetic valve can be implanted within the native mitral valve in a transapical procedure, whereby the prosthetic valve (on the distal end portion of the delivery apparatus) is introduced into the left ventricle through a surgical opening in the chest and the apex of the heart and the prosthetic valve is positioned within the native mitral valve.

For implanting a prosthetic valve within the native tricuspid valve, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, and into the right atrium, and the prosthetic valve is positioned within the native tricuspid valve. A similar approach can be used for implanting the prosthetic valve within the native pulmonary valve or the pulmonary artery, except that the prosthetic valve is advanced through the native tricuspid valve into the right ventricle and toward the pulmonary valve/pulmonary artery.

Another delivery approach is a transatrial approach whereby a prosthetic valve (on the distal end portion of the delivery apparatus) is inserted through an incision in the chest and an incision made through an atrial wall (of the right or left atrium) for accessing any of the native heart valves. Atrial delivery can also be made intravascularly, such as from a pulmonary vein. Still another delivery approach is a transventricular approach whereby a prosthetic valve (on the distal end portion of the delivery apparatus) is inserted through an incision in the chest and an incision made through the wall of the right ventricle (typically at or near the base of the heart) for implanting the prosthetic valve within the native tricuspid valve, the native pulmonary valve, or the pulmonary artery.

In all delivery approaches, the delivery apparatus can be advanced over a guidewire previously inserted into a patient's vasculature. Moreover, the disclosed delivery approaches are not intended to be limited. Any of the prosthetic valves disclosed herein can be implanted using any of various delivery procedures and delivery devices known in the art.

General Considerations

It should be understood that the disclosed embodiments can be adapted for delivering and implanting prosthetic devices in any of the native annuluses of the heart (e.g., the aortic, pulmonary, mitral, and tricuspid annuluses), and can be used with any of various delivery devices for delivering the prosthetic valve using any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic valve comprising: a radially expandable and compressible frame comprising a plurality of interconnected struts; a valvular structure comprising a plurality of leaflets configured to regulate the flow of blood through the prosthetic valve, the leaflets having undulating cusp edge portions; and at least one connecting skirt having a shape that corresponds to the cusp edge portion of at least one leaflet; wherein the connecting skirt connects the cusp edge portion of the leaflet to at least one of the struts of the frame; wherein the connecting skirt comprises a first set of yarns intersecting with a second set of yarns, wherein the first and second sets of yarns extend at oblique angles relative to a longitudinal axis of the at least one strut.

Example 2. The prosthetic valve of any example herein, particularly example 1, wherein the first set of yarns are perpendicular to the second set of yarns.

Example 3. The prosthetic valve of any example herein, particularly any one of examples 1-2, wherein the first set of yarns are woven with the second set of yarns.

Example 4. The prosthetic valve of any example herein, particularly any one of examples 1-3, wherein the first set of yarns extend at an angle between about 40 and 50 degrees relative to the longitudinal axis of the at least one strut.

Example 5. The prosthetic valve of any example herein, particularly example 4, wherein the angle is about 45 degrees.

Example 6. The prosthetic valve of any example herein, particularly any one of examples 1-5, wherein a first longitudinal edge portion of the connecting skirt is coupled to the cusp edge portion of the leaflet, and a second longitudinal edge portion of the connecting skirt is coupled to the at least one strut, the second edge portion being opposite the first edge portion.

Example 7. The prosthetic valve of any example herein, particularly example 6, wherein the second edge portion of the connecting skirt is sutured to the at least one strut.

Example 8. The prosthetic valve of any example herein, particularly any one of examples 6-7, wherein the second edge portion of the connecting skirt is configured to overlay at least a portion of an inner surface of the at least one strut.

Example 9. The prosthetic valve of any example herein, particularly example 8, wherein the second edge portion of the connecting skirt has a plurality of flaps that extend at least partially around the at least one strut.

Example 10. The prosthetic valve of any example herein, particularly any one of examples 6-9, wherein the first edge portion of the connecting skirt extends along an entire length of the cusp edge portion of the leaflet.

Example 11. The prosthetic valve of any example herein, particularly any one of examples 6-10, wherein the first edge portion of the connecting skirt, the cusp edge portion of the leaflet, and a reinforcing cord extending along the cusp edge portion of the leaflet are coupled together by one or more stitches.

Example 12. The prosthetic valve of any example herein, particularly any one of examples 1-11, wherein the connecting skirt is one of a plurality of connecting skirts, wherein each connecting skirt connects a corresponding leaflet to a respective strut adjacent to the connecting skirt.

Example 13. The prosthetic valve of any example herein, particularly any one of examples 1-12, wherein the longitudinal axis of the at least one strut extends at an oblique angle relative to a central longitudinal axis of the frame.

Example 14. A prosthetic valve comprising: a radially expandable and compressible frame comprising a plurality of interconnected struts, wherein the frame comprises an inflow end and an outflow end; a valvular structure comprising a plurality of leaflets configured to regulate the flow of blood through the prosthetic valve, the leaflets having undulated cusp edge portions; and a connecting skirt having undulated shape that corresponds to a shape of the cusp edge portions; wherein the connecting skirt connects the cusp edge portions of the plurality of leaflets to struts of the frame that extend diagonally relative to the inflow and outflow ends of the frame; wherein the connecting skirt comprises a first set of yarns interwoven with a second set of yarns, wherein the first set of yarns extend at an oblique angle relative to the struts connected to the connecting skirt.

Example 15. The prosthetic valve of any example herein, particularly example 14, wherein the connecting skirt comprises a plurality of skirt segments, each skirt segment connecting a corresponding cusp edge portion of a leaflet to a respective strut.

Example 16. The prosthetic valve of any example herein, particularly any one of examples 14-15, wherein the first set of yarns are perpendicular to the second set of yarns.

Example 17. The prosthetic valve of any example herein, particularly any one of examples 14-16, wherein the oblique angle is between about 40 and 50 degrees.

Example 18. The prosthetic valve of any example herein, particularly example 17, wherein the oblique angle is about 45 degrees.

Example 19. The prosthetic valve of any example herein, particularly any one of examples 14-18, wherein a first longitudinal edge portion of the connecting skirt is coupled to the cusp edge portions of the leaflets, and a second longitudinal edge portion of the connecting skirt is coupled to the struts, the second edge portion being opposite the first edge portion.

Example 20. The prosthetic valve of any example herein, particularly example 19, wherein the second edge portion of the connecting skirt is sutured to the struts.

Example 21. The prosthetic valve of any example herein, particularly any one of examples 19-20, wherein the second edge portion of the connecting skirt is configured to overlay at least a portion of an inner surface of the struts.

Example 22. The prosthetic valve of any example herein, particularly any one of examples 19-21, wherein the first edge portion of the connecting skirt extends along an entire length of the cusp edge portions of the leaflets.

Example 23. The prosthetic valve of any example herein, particularly any one of examples 19-22, wherein the first edge portion of the connecting skirt, the cusp edge portions of the leaflets, and one or more reinforcing cords extending along the cusp edge portions of the leaflets are coupled together by one or more stitches.

Example 24. A method for mounting a valvular structure comprising a plurality of leaflets to a radially expandable and compressible frame, the method comprising: coupling at least one leaflet to a connecting skirt; and coupling the connecting skirt to a strut of the frame that extends diagonally along a line extending from an inflow end of the frame to an outflow end of the frame; wherein the connecting skirt comprises a first set of yarns interwoven with a second set of yarns, wherein the connecting skirt is oriented such that the first set of yarns extend at an oblique angle relative to a longitudinal axis of the strut.

Example 25. The method of any example herein, particularly example 24, further comprising coupling the plurality of leaflets to a plurality of connecting skirts, and coupling the plurality of connecting skirts to respective struts of the frame, wherein the leaflets have undulated cusp edge portions and the connecting skirts form an undulating shape that corresponds to the undulated cusp edge portions of the leaflets.

Example 26. The method of any example herein, particularly any one of examples 24-25, wherein the first set of yarns are perpendicular to the second set of yarns.

Example 27. The method of any example herein, particularly any one of examples 24-26, wherein the oblique angle is between about 40 and 50 degrees.

Example 28. The method of any example herein, particularly example 27, wherein the oblique angle is about 45 degrees.

Example 29. The method of any example herein, particularly any one of examples 24-28, wherein coupling the leaflet to the strut comprises coupling a first longitudinal edge portion of the connecting skirt to the cusp edge portion of the leaflet, and coupling a second longitudinal edge portion of the connecting skirt to the strut, the second edge portion being opposite the first edge portion.

Example 30. The method of any example herein, particularly example 29, wherein the second edge portion of the connecting skirt is sutured to the strut.

Example 31. The method of any example herein, particularly any one of examples 29-30, wherein the second edge portion of the connecting skirt is configured to overlay at least a portion of an inner surface of the strut.

Example 32. The method of any example herein, particularly any one of examples 29-31, wherein the second edge portion of the connecting skirt comprises a plurality of flaps, wherein each flap couples a segment of the cusp edge portion to a respective strut adjacent to the segment of the cusp edge portion.

Example 33. The method of any example herein, particularly any one of examples 29-32, wherein the first edge portion of the connecting skirt extends along an entire length of the cusp edge portion of the leaflet.

Example 34. The method of any example herein, particularly any one of examples 29-33, wherein coupling the leaflet to the strut comprises coupling the first edge portion of the connecting skirt, the cusp edge portion of the leaflets, and a reinforcing cord extending along the cusp edge portion of the leaflet together by one or more stitches.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

The invention claimed is:

1. A prosthetic valve comprising:

a radially expandable and compressible frame comprising a plurality of interconnected struts;

a valvular structure comprising a plurality of leaflets configured to regulate the flow of blood through the prosthetic valve, the leaflets having undulating cusp edge portions; and at least one connecting skirt having a shape that corresponds to the cusp edge portion of at least one leaflet;

wherein the connecting skirt connects the cusp edge portion of the leaflet to at least one of the struts of the frame;

wherein the connecting skirt comprises a first set of yarns intersecting with a second set of yarns, wherein the first and second sets of yarns extend at oblique angles relative to a longitudinal axis of the at least one strut;

wherein a first longitudinal edge portion of the connecting skirt is coupled to the cusp edge portion of the leaflet, and a second longitudinal edge portion of the connecting skirt is coupled to the at least one strut, the second edge portion being opposite the first edge portion.

2. The prosthetic valve of claim 1, wherein the first set of yarns are perpendicular to the second set of yarns.

3. The prosthetic valve of claim 1, wherein the first set of yarns are woven with the second set of yarns.

4. The prosthetic valve of claim 1, wherein the first set of yarns extend at an angle between about 40 and 50 degrees relative to the longitudinal axis of the at least one strut.

5. The prosthetic valve of claim 4, wherein the angle is about 45 degrees.

6. The prosthetic valve of claim 1, wherein the second edge portion of the connecting skirt is sutured to the at least one strut.

7. The prosthetic valve of claim 1, wherein the second edge portion of the connecting skirt is configured to overlay at least a portion of an inner surface of the at least one strut.

8. The prosthetic valve of claim 7, wherein the second edge portion of the connecting skirt has a plurality of flaps that extend at least partially around the at least one strut.

9. The prosthetic valve of claim 1, wherein the first edge portion of the connecting skirt extends along an entire length of the cusp edge portion of the leaflet.

10. The prosthetic valve of claim 1, wherein the first edge portion of the connecting skirt, the cusp edge portion of the leaflet, and a reinforcing cord extending along the cusp edge portion of the leaflet are coupled together by one or more stitches.

11. The prosthetic valve of claim 1, wherein the connecting skirt is one of a plurality of connecting skirts, wherein each connecting skirt connects a corresponding leaflet to a respective strut adjacent to the connecting skirt.

12. The prosthetic valve of claim 1, wherein the longitudinal axis of the at least one strut extends at an oblique angle relative to a central longitudinal axis of the frame.

13. A prosthetic valve comprising:

a radially expandable and compressible frame comprising a plurality of interconnected struts, wherein the frame comprises an inflow end and an outflow end;

a valvular structure comprising a plurality of leaflets configured to regulate the flow of blood through the prosthetic valve, the leaflets having undulated cusp edge portions; and a connecting skirt having undulated shape that corresponds to a shape of the cusp edge portions;

wherein the connecting skirt connects the cusp edge portions of the plurality of leaflets to struts of the frame that extend diagonally relative to the inflow and outflow ends of the frame;

wherein the connecting skirt comprises a first set of yarns interwoven with a second set of yarns, wherein the first set of yarns extend at an oblique angle relative to the struts connected to the connecting skirt.

14. The prosthetic valve of claim 13, wherein the connecting skirt comprises a plurality of skirt segments, each skirt segment connecting a corresponding cusp edge portion of a leaflet to a respective strut.

15. A method for mounting a valvular structure comprising a plurality of leaflets to a radially expandable and compressible frame, the method comprising:

coupling at least one leaflet to a connecting skirt; and coupling the connecting skirt to a strut of the frame that extends diagonally along a line extending from an inflow end of the frame to an outflow end of the frame;

wherein the connecting skirt comprises a first set of yarns interwoven with a second set of yarns, wherein the connecting skirt is oriented such that the first set of yarns extend at an oblique angle relative to a longitudinal axis of the strut;

wherein coupling the leaflet to the connecting skirt comprises coupling a first longitudinal edge portion of the connecting skirt to the cusp edge portion of the leaflet, and coupling the connecting skirt to the strut of the frame comprises coupling a second longitudinal edge portion of the connecting skirt to the strut, the second edge portion being opposite the first edge portion.

16. The method of claim 15, further comprising coupling the plurality of leaflets to a plurality of connecting skirts, and coupling the plurality of connecting skirts to respective struts of the frame, wherein the leaflets have undulated cusp edge portions and the connecting skirts form an undulating shape that corresponds to the undulated cusp edge portions of the leaflets.

17. The method of claim 15, wherein the second edge portion of the connecting skirt comprises a plurality of flaps, wherein each flap couples a segment of the cusp edge portion to a respective strut adjacent to the segment of the cusp edge portion.

18. The method of claim 15, wherein coupling the leaflet to the strut comprises coupling the first edge portion of the connecting skirt, the cusp edge portion of the leaflets, and a reinforcing cord extending along the cusp edge portion of the leaflet together by one or more stitches.

* * * * *